United States Patent
Wong et al.

[11] Patent Number: 6,080,362
[45] Date of Patent: Jun. 27, 2000

[54] POROUS SOLID REMEDIATION UTILIZING PULSED ALTERNATING CURRENT

[75] Inventors: Sik-Lam Wong, San Leandro; James Howard Shea, Castro Valley, both of Calif.

[73] Assignee: Maxwell Technologies Systems Division, Inc., San Diego, Calif.

[21] Appl. No.: 09/041,589

[22] Filed: Mar. 12, 1998

Related U.S. Application Data

[62] Division of application No. 08/481,172, Jun. 7, 1995, Pat. No. 5,756,054.

[51] Int. Cl.[7] .................. A61L 2/00; A61L 2/03
[52] U.S. Cl. .................. 422/29; 422/32; 424/40; 424/405; 424/613; 47/58.2; 47/DIG. 10
[58] Field of Search .................. 47/58.1, DIG. 10; 422/29, 32; 588/205; 424/40, 613, 405

[56] References Cited

U.S. PATENT DOCUMENTS

| | | | |
|---|---|---|---|
| 3,702,973 | 11/1972 | Daugherty et al. | 331/94.5 |
| 3,710,163 | 1/1973 | Bomko et al. | 313/63 |
| 3,796,906 | 3/1974 | Henry-Bezy et al. | 315/5.41 |
| 3,883,413 | 5/1975 | Douglas-Hamilton | 204/176 |
| 3,921,002 | 11/1975 | Williams et al. | 250/533 |
| 3,956,634 | 5/1976 | Tran et al. | 250/396 |
| 3,963,625 | 6/1976 | Lowther | 250/533 |
| 4,076,617 | 2/1978 | Bybel et al. | 210/19 |
| 4,131,528 | 12/1978 | Tsujimoto et al. | 204/157.1 |
| 4,167,466 | 9/1979 | Orr, Jr. et al. | 204/176 |
| 4,315,837 | 2/1982 | Rourke et al. | 252/430 |
| 4,339,783 | 7/1982 | Kinashi et al. | 361/235 |
| 4,614,573 | 9/1986 | Masuda | 204/176 |
| 4,666,480 | 5/1987 | Mann | 62/11 |
| 5,089,098 | 2/1992 | Tacchi | 204/176 |
| 5,100,521 | 3/1992 | Schwarzl | 204/176 |
| 5,116,574 | 5/1992 | Pearson | 422/3 |
| 5,141,722 | 8/1992 | Nagashima | 422/292 |
| 5,158,654 | 10/1992 | Yoshimoto et al. | 204/59 |
| 5,232,882 | 8/1993 | Yoshimoto et al. | 502/5 |
| 5,332,555 | 7/1994 | Hosokawa et al | 422/186.05 |
| 5,368,816 | 11/1994 | Detzer | 422/28 |
| 5,370,846 | 12/1994 | Yokomi et al. | 422/186.07 |
| 5,378,898 | 1/1995 | Schonberg et al. | 250/492.3 |
| 5,409,616 | 4/1995 | Garbutt et al. | 210/760 |
| 5,451,388 | 9/1995 | Chen et al. | 423/240 |
| 5,566,627 | 10/1996 | Pryor | 111/118 |
| 5,578,280 | 11/1996 | Kazi et al. | 422/186.07 |
| 5,624,734 | 4/1997 | Rees et al. | 422/186.11 |
| 6,007,770 | 12/1999 | Peiper et al. | 422/22 |

FOREIGN PATENT DOCUMENTS

| | | | |
|---|---|---|---|
| 2-177845 | 7/1990 | Japan | 47/DIG. 10 |
| 441013 | 12/1974 | U.S.S.R. | 47/DIG. 10 |
| 485720 | 1/1976 | U.S.S.R. | 47/DIG. 10 |
| 719523 | 2/1980 | U.S.S.R. | 47/DIG. 10 |
| 1551598 A1 | 3/1990 | U.S.S.R. | 422/29 |

OTHER PUBLICATIONS

"Ozone Generation by Pulsed Corona Discharge in a Wire Cylinder Arrangement," by I.D. Chambers, L. Zanella, S.J. MacGregor and J.A. Wray, article appearing in (1994) The Institution of Electrical Engineers, printed and published by the IEEE, Savoy Place, London WC2R, U.K. at pp. 611–614.

*Primary Examiner*—Steven P. Griffin
*Assistant Examiner*—Timothy C Vanoy
*Attorney, Agent, or Firm*—Gregory S. Rosenblatt; Wiggin & Dana

[57] ABSTRACT

A method to disinfect a porous solid medium, such as soil, includes the steps of embedding a plurality of electrodes into the porous solid medium and applying a plurality of alternating current voltage pulses between the electrodes. The voltage pulses have a peak voltage of at least 10 kilovolts and are of an intensity and duration effective to generate a quantity of ozone. The ozone is produced in quantities sufficient to disinfect the porous solid medium.

7 Claims, 3 Drawing Sheets

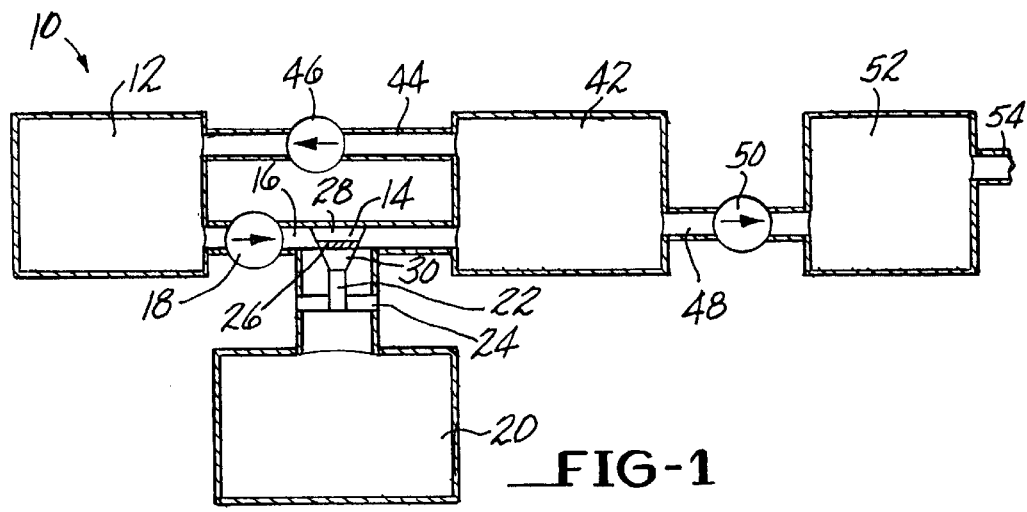
FIG-1
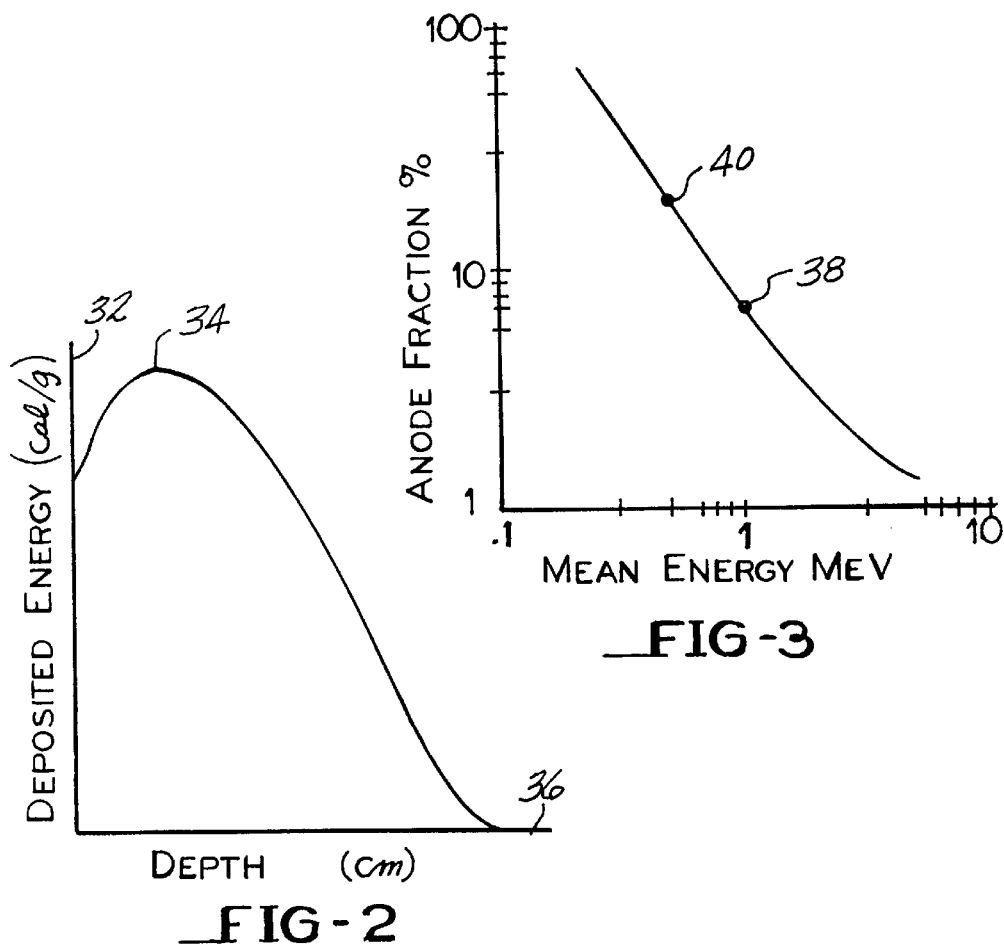
FIG-2
FIG-3

POROUS SOLID REMEDIATION UTILIZING PULSED ALTERNATING CURRENT

This is a Division of application Ser. No. 08/481,172, that was filed on Jun. 7, 1995, U.S. Pat. No. 5,756,054, and incorporated herein by reference in its entirety.

BACKGROUND OF THE INVENTION

This invention relates to a generator for the production of ozone and the use of ozone for bioremediation. More particularly, an ozone generator utilizes a cryogenic oxygen source or a pulsed power supply to enhance ozone production. The ozone is used to convert volatile organic compounds in the air, liquid or the soil to innocuous compounds.

Ozone ($O_3$) is a strong oxidizer that is used to convert harmful organic compounds into innocuous compounds. U.S. Pat. No. 4,076,617 to Bybel et al. discloses a system for the remediation of liquid waste. Ultrasonic waves break up solid particles suspended in the liquid waste and the fine particles then form an emulsion in the liquid. An ozone stream is passed through the emulsion oxidizing the organic contaminants.

In U.S. Pat. No. 4,076,617, the ozone is formed by passing dry oxygen or dry air through a corona discharge grid. The ozone yield is disclosed to be from about 3% to about 6%. The remainder of the gas recombines to form oxygen or nitrogen compounds.

U.S. Pat. No. 5,409,616 to Garbutt et al. discloses an ozone generator containing a molecular sieve to increase the oxygen content from about 20% (in ambient air) to in excess of 85% and to extract moisture from the gas. An alternating current power supply connected to a 5000 volt alternating current transformer converts the oxygen to ozone.

Both the Bybel et al. and Garbutt et al. patents are incorporated by reference in their entireties herein.

Ozone has been utilized for the bioremediation of organic compounds suspended or dissolved in a liquid medium. The ozone is bubbled through the liquid medium and, to enhance the surface area of the ozone bubbles, bubble breaking spargers have been utilized. However, to the best of our knowledge, ozone has not been successfully applied to the bioremediation of either a gaseous medium or a solid medium.

There is a need to disinfect gaseous media, such as the air in a hospital of germs and viruses or the air of a laboratory of volatile organic compounds. Presently, the air in these environments is not recirculated, but is discharged through a filter to the outside environment. This method presents the potential for releasing harmful compounds to the outside environment. Further, any energy applied to heat or cool that air is lost when the air is discharged.

Ozone has not been applied to the remediation of air because the concentration of contaminants is usually low and it has proven difficult to ensure contact between the ozone and the contaminants without providing high concentrations of ozone. High concentrations of ozone are both expensive and potentially hazardous.

Porous solids, such as soil, are usually remediated of fungi through the application of a fungicide such as dimethyl bromide. The fungicides are typically toxic. Ozone would be an environmentally sound replacement for the fungicides. The strong oxidizing of the ozone could convert the soil contaminants to relatively innocuous compounds and the ozone is unstable, so that when released to the air, it would rapidly convert to oxygen.

There remains, therefore, a need for both an ozone generator with enhanced ozone output and a mechanism to apply the ozone for the bioremediation of gaseous and porous solid media.

SUMMARY OF THE INVENTION

Accordingly, an object of one embodiment of the invention is to provide an ozone generator with enhanced output. It is a feature of this embodiment that cryogenic oxygen is irradiated either by a repetitively pulsed electron beam accelerator or by a repetitively pulsed corona discharge. It is an advantage of this embodiment that the cryogenic oxygen is readily separated from ozone by exploiting either the density or the vapor point differential. The use of a pulsed energy source maximizes the energy utilized for ozone generation rather than converted into heat.

It is an object of a second embodiment of the invention to utilize ozone to remove biological and organic contaminants from either a gaseous medium or from a porous solid medium. It is a feature of this embodiment that the gaseous medium is passed through a reaction chamber that contains an inert material to increase the surface area available for the reaction between ozone and the contaminants. When the medium is a porous solid, the application of a pulsed alternating current electric field between electrodes embedded in the porous solid medium ozone generates ozone in interspersed air filled pores. The ozone diffuses to the surface of the medium, and on entering the atmosphere, can be converted to oxygen via a conventional technique such as exposure to activated carbon, heat or ultra violet light.

In accordance with the invention, there is provided, in one embodiment of the invention, an ozone generator. The ozone generator includes a source of cryogenic oxygen. A first conduit delivers the cryogenic oxygen to an irradiation chamber. In the irradiation chamber, a portion of the cryogenic oxygen is converted into ozone. An ozone separator separates the ozone from the cryogenic oxygen.

In accordance with a second embodiment of the invention, there is provided a method for the destruction of organic material in a porous solid medium. A plurality of electrodes are embedded into the porous medium. A plurality of alternating voltage pulses are applied between the electrodes. The voltage pulses are of an intensity and duration effective to generate a quantity of ozone in the porous medium that is effective to destroy the organic medium.

The above stated objects, features and advantages will become more apparent to those skilled in the art from the specification and drawings that follow.

IN THE DRAWINGS

FIG. 1 illustrates an ozone generator in accordance with the invention.

FIG. 2 graphically illustrates the relationship between the intensity of an electron beam and the depth of penetration of electrons emerging from an anode.

FIG. 3 graphically illustrates the relationship between the electron beam intensity and the depth of penetration of electrons emerging from a titanium anode.

FIG. 4 illustrates a condensation chamber for separating ozone from oxygen.

FIG. 5 graphically illustrates a voltage pulse effective for the generation of ozone.

DETAILED DESCRIPTION OF THE DRAWINGS

Figure 4:
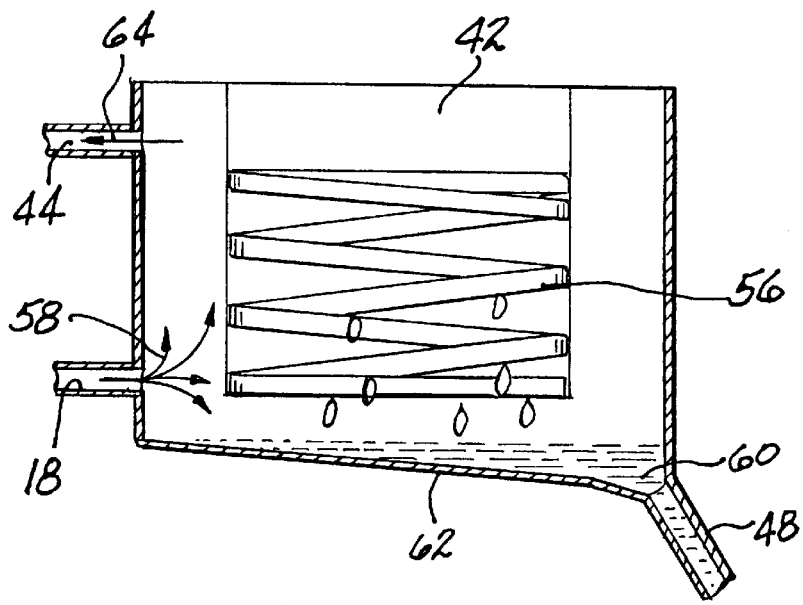

FIG. 1 illustrates in block diagram an ozone generator 10 in accordance with the invention. The ozone generator 10 includes a cryogenic oxygen source 12 that can be any commercial unit for the production of liquid oxygen. Cryogenic oxygen is delivered to an irradiation chamber 14 through a first conduit 16. A pump 18 delivers a desired volume of cryogenic oxygen at a desired flow rate.

The cryogenic oxygen is delivered to the irradiation chamber 14 either as a liquid, at a temperature below the boiling point of oxygen (90K), or as a cryogenic gas, below the boiling point of ozone (161K).

In one embodiment of the invention, the power supply 20 is a repetitively pulsed electron beam accelerator such as a linear accelerator, a compact linear induction accelerator, a van de Graf accelerator or a Marx circuit with a pulse forming network. More detailed descriptions of such devices are found in U.S. Pat. Nos. 3,702,973 to Daugherty et al., 3,883,413 to Douglas-Hamilton and 3,956,634 to Tran et al. all of which are incorporated by reference in their entireties herein.

The power supply 20 delivers a stream of electrons through an electron gun 22 focused by a collimator 24 such as an adjustable magnetic ring. The electron stream impacts a target anode 26 that forms a front wall of the first conduit 16. Most of the electrons pass through the anode 26 and into the first conduit 16 irradiating the flowing oxygen.

The irradiation chamber 14 is defined by the anode 26, a back wall 28 of the first conduit 16 and the diverging walls 30 of the electron stream. The irradiation chamber 14 is sized such that it has an areal density about equal to the maximum depth of penetration of the electrons emerging from the anode 26. The areal density is equal to the density ($g/cm^3$) times the depth (cm) of the irradiation chamber. As shown in FIG. 2, the energy deposited on the flowing stream of oxygen, axis 32, achieves a maximum 34 when penetrating an anode foil having a relatively thin cross-sectional thickness, axis 36.

The maximum value is dependent on the anode material and the electron beam intensity. FIG. 3 illustrates that for a titanium foil anode with a thickness of 0.002 inch to 0.003 inch, only about 5% of the electron energy is lost when the electron beam is operated at 1 megavolt, reference point 38, and less than 10% is lost when the operating voltage is 0.6 megavolt, reference point 40.

Referring back to FIG. 1, in one embodiment, the power source 20 is a compact linear induction accelerator operating at a voltage of from about 0.5 megavolt to about 10 megavolts and preferably operating at a voltage of from about 0.8 megavolt to about 1.2 megavolts with the optimal operating voltage dependent on the throughput rate of the cryogenic oxygen. The energy produced by the compact linear induction accelerator is about 230 joules per pulse at an operating voltage of about 0.6 megavolt with a pulse rate of from about 50 to about 150 pulses per second. The optimal voltage repetition rate is determined experimentally. The rate is dependent on the desired flow rate, the ozone concentration and other operating parameters.

When the cryogenic oxygen source 12 provides liquid oxygen to the irradiation chamber 14, ozone concentrations up to 33%, by volume, are possible by irradiation of the liquid oxygen. The 33% maximum is determined by the equilibrium point at which the ionization rate of ozone molecules is equal to that of the oxygen molecules, the number of electrons associated with ozone molecules is equal to the number of electrons associated with oxygen molecules.

Full conversion of all oxygen molecules to ozone molecules requires an energy of 717 calories per gram so that to obtain a product with 33% ozone, a accumulated dose of 240 cal/gm is required. This is equal to approximately 40 pulses from the compact linear induction accelerator requiring that the liquid oxygen dwell in the irradiation chamber for approximately 0.4 seconds. Accordingly, the cross-sectional area of the irradiation chamber and the flow rate generated by first pump 18 are selected such that the flowing oxygen is within the irradiation chamber for a time of from about 0.3 to about 1 second and preferably, for a time of from about 0.35 to about 0.5 seconds.

One advantage of irradiating the oxygen at cryogenic temperatures is the capability to exploit the boiling point and/or density differences between ozone and oxygen. For example, as cryogenic gases, the density of ozone is 1.5 times the density of oxygen.

As a further advantage, if liquid oxygen is employed, the thermal conductivity of liquid oxygen is greater than that of gaseous oxygen enhancing cooling of the anode.

The irradiated cryogenic oxygen flows to an ozone concentrator 42 where the ozone is separated from residual oxygen. Ozone has a higher density than oxygen so, in one embodiment, the ozone concentrator 42 is a static flow chamber where the liquid ozone gravimetrically separates from the liquid oxygen. The liquid oxygen is recycled through a second conduit 44, driven by a pump 46 back to the cryogenic oxygen source 20. The ozone is drawn off through a third conduit 48, optionally driven by a pump 50, and delivered to a vaporization unit 52 where the liquid ozone is converted into ozone gas and stored until dispensed through an output conduit 54.

If the cryogenic oxygen/ozone mixture is delivered to the ozone concentrator 42 at a temperature of between 90K and 161K, between the boiling point of oxygen and the boiling point of ozone, a condensation coil 56, as illustrated in FIG. 4, having a temperature between 91K and 160K may be utilized to condense the ozone. The first conduit 18 delivers a gaseous mix 58 of oxygen and ozone to the ozone concentrator 42. This temperature range may be achieved by providing the cryogenic oxygen to the irradiation chamber as a gas in this temperature range or by heating the liquid mixture of oxygen and ozone downstream of the irradiation chamber to this temperature range. The gaseous mix 58 contacts the condensation coil 56. The ozone condenses to a liquid 60 along a bottom surface 62 of the ozone concentrator 42 and is drawn off through the third conduit 48. Gaseous oxygen 64 returns through the second conduit 44 to the cryogenic oxygen source.

Alternatively, referring back to FIG. 1, the power supply 20 and the electron gun may be replaced by a pulsed corona discharge apparatus that typically uses pulsed high voltage. One such corona discharge apparatus, for a different application, is disclosed in U.S. Pat. No. 4,339,783 to Kinashi et al. that is incorporated by reference in its entirety herein. To maximize ozone generation and to minimize wasted energy, the voltage is provided as a series rapid pulses. Instead of liquid oxygen, in this embodiment, gaseous oxygen at a temperature between 90K and 161K is used in the reactor chamber.

Figure 5:
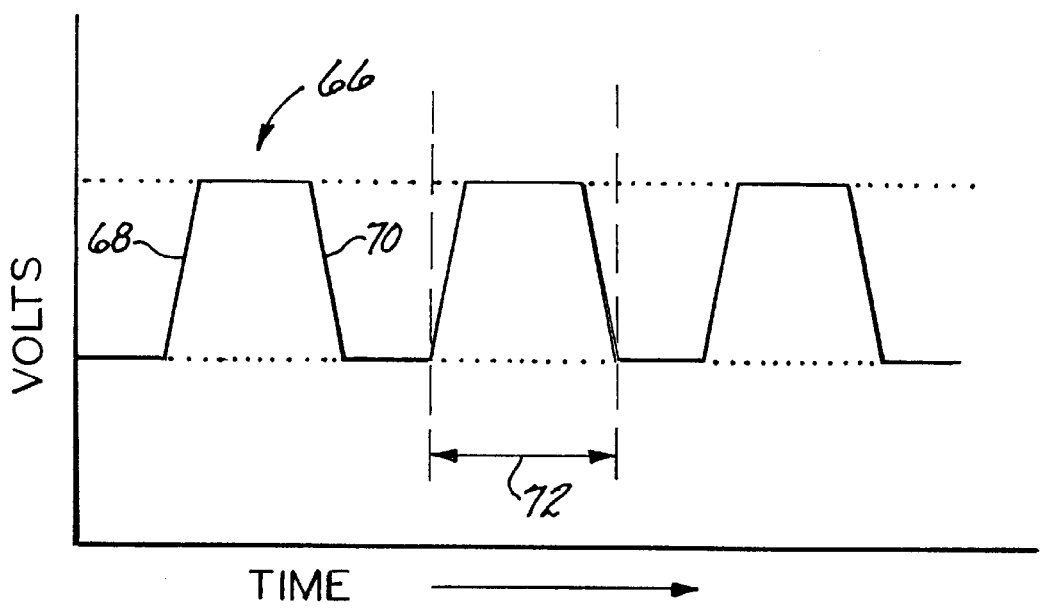

As illustrated in FIG. 5, the pulsed source varies between a base line voltage of zero volts and a peak voltage of at least 10 kilovolts and potentially up to 750 kilovolts. The voltage pulses 66 utilize a fast rise time 68. The rise time 68 is shorter than the delay in coronal onset. The delay in coronal onset is defined as the time required for an electric arc to form between a high voltage electrode and a ground. By having the rise time shorter than the coronal onset, the strength of the electric field applied to the irradiation chamber 14 is maximized. Preferably, the rise time is from about 2 nanoseconds to about 80 nanoseconds and most preferably, from about 2 nanoseconds to about 20 nanoseconds.

The fall time 70 is relatively short to minimize energy not used for ozone generation. The fall time 70 is from about 2 nanoseconds to about 100 nanoseconds and preferably from about 2 nanoseconds to about 20 nanoseconds. The pulse width 72, as well as the repetition rate are optimized for each corona discharge reactor design and gas flow rate. For the design illustrated in FIG. 1 and an oxygen flow rate of 1 standard ft$^3$/min., a preferred pulse width is from about 20 nanoseconds to about 100 nanoseconds and a preferred repetition rate is from 20 per second to about 500 per second.

Figure 6:
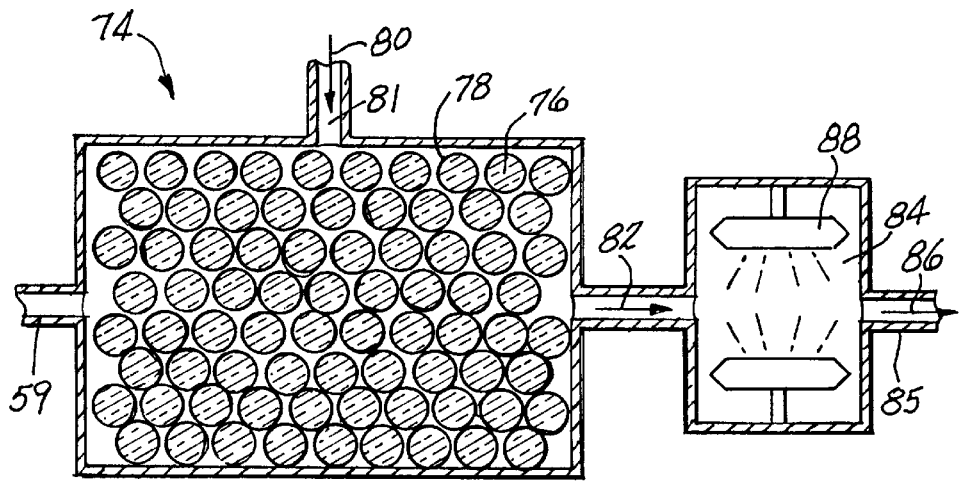
FIG. 6 illustrates a chamber for the purification of a gaseous medium.

FIG. 6 illustrates a reaction chamber 74 effective to disinfect air containing biological contaminants such as germs or viruses, as well as volatile organic compounds such as organic solvents from a gaseous medium such as hospital or laboratory air. The reaction chamber 74 is a hermetic enclosure having a first inlet through which an ozone stream is introduced, such as from the output conduit 54 of the ozone generator of FIG. 1. Contained within the reaction chamber 74 is a surface area increasing medium 76 such as inert beads of glass or ceramics. The outside diameter of the inert beads is optimized for disinfecting efficiency and typically will range from about 1 mm to about 10 mm. The inert beads increase the surface area inside the reaction chamber by several factors of magnitude. The beads 76 may be coated with a suitable catalyst 78 to promote the oxidation reaction. One suitable catalyst is titanium oxide.

The ozone reacts with the biological and organic compounds and renders them environmentally innocuous. The size of the reaction chamber 74 and the rate of flow of air 80 through a second inlet 81 into the reaction chamber are selected to be effective to provide sufficient time in the reaction chamber for complete air disinfection and cleaning. Typically, a dwell time within the reaction chamber 74 is from about 1 second to about 60 seconds and preferably from about 3 seconds to about 20 seconds.

In a closed environment such as a hospital or laboratory, even trace amounts of ozone may constitute an irritant to occupants. Accordingly, the output 82 is preferably directed to an ozone destroying chamber 84 through outlet 85 before being recirculated 86 into the hospital or laboratory environment. Located within the ozone destroying chamber 84 is any device effective to promote the conversion of $O_3$ back to $O_2$ such as heating coils or an ultraviolet light source 88.

Figure 7:
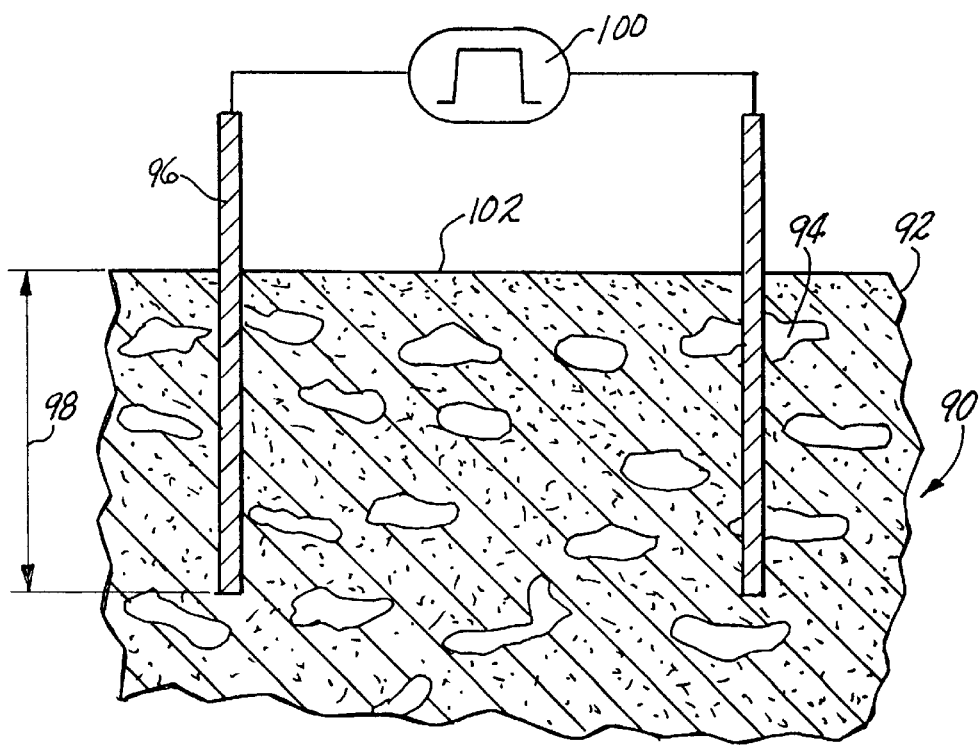
FIG. 7 illustrates a system for the purification of a porous solid medium.

The pulsed electric field illustrated in FIG. 5 is effective to disinfect a porous solid medium by the method illustrated in FIG. 7. A porous solid medium 90 includes a solid component 92 interspersed with air pockets 94. Typical porous solid media include soil, sand and cinder block.

A plurality of electrodes 96 are embedded into the porous solid media 90. The depth 98 is determined by the depth of disinfection required as well as the power available to be applied to the electrodes. For a pair of electrodes 96 having a surface area of 10 cm$^2$ and spaced apart by a distance of 2 cm utilizing a 50 kilovolt alternating current pulse power supply 100, a depth 98 can be satisfactorily disinfected in less than 10 minutes.

The alternating current power supply 100 provides a plurality of alternating current voltage pulses between the electrode 96. The voltage pulses are of an intensity and duration that is effective to generate a quantity of ozone in the air pockets 94. The ozone disinfects organic material in the solid component 92 as it migrates to the surface 102 where it diffuses to the air and can be converted back to oxygen by standard techniques such as exposure to heat, ultra violet light and/or activated carbon.

An effective voltage applied by the alternating current power supply 100 is from about zero volts as the baseline to from 10 to 200 kilovolts as the peak voltage. Suitable voltage pulse widths are from about 0.02 milliseconds to about 20 milliseconds with a frequency of from about 50 pulses per second to 50,000 pulses per second. The alternating current voltage is applied to the electrodes for a time of from about 2 seconds to about 5 minutes to effectively disinfect the porous solid medium. The peak voltage, repetition rate, pulse width, gas species and duration of application are determined by the condition and the amount of porous solid medium to be disinfected.

It is apparent that there has been provided in accordance with this invention an ozone generator having enhanced ozone production capacity and systems to utilized ozone for bioremediation that fully satisfy the objects, features and advantages set forth hereinbefore. While the invention has been described in combination with specific embodiments and examples thereof, it is evident that many alternatives, modifications and variations will be apparent to those skilled in the art in light of the foregoing description. Accordingly, it is intended to embrace all such alternatives, modifications and variations as fall within the spirit and broad scope of the appended claims.

We claim:

1. A method to disinfect a porous solid medium, comprising the steps of:

embedding a plurality of electrodes into said porous solid medium;

applying a plurality of alternating current voltage pulses between said electrodes wherein each of said voltage pulses has a peak voltage of from 10 kilovolts to 200 kilovolts and said plurality of alternating current voltage pulses are of an intensity and duration effective to generate a quantity of ozone in said porous solid medium that is effective to disinfect said porous solid medium.

2. The method of claim 1 wherein said duration is between 2 seconds and 5 minutes.

3. The method of claim 1 wherein said porous solid medium is selected to be soil.

4. The method of claim 3 wherein said soil contains fungi that are destroyed by said method.

5. The method of claim 1 wherein the pulse width of the alternating current voltage is between about 0.02 milliseconds and about 0.02 seconds.

6. The method of claim 5 wherein said pulse frequency of the alternating current voltage is between about 50 per second and 50,000 per second.

7. The method of claim 1 wherein said pulse frequency of the alternating current voltage is between about 50 per second and about 50,000 per second.

* * * * *